United States Patent
Wood

[11] 3,970,847
[45] July 20, 1976

[54] DIMENSION MEASURING APPARATUS

[76] Inventor: John Keith Wood, 147 Prescot Road, Aughton, Ormskirk, England

[22] Filed: Dec. 13, 1974

[21] Appl. No.: 532,440

[30] Foreign Application Priority Data
Dec. 21, 1973 United Kingdom............... 59366/73

[52] U.S. Cl................................ 250/234; 250/560; 356/156
[51] Int. Cl.² .......................................... H01J 3/14
[58] Field of Search.................... 250/234, 235, 560; 356/157, 159, 167, 156

[56] References Cited
UNITED STATES PATENTS

| | | | |
|---|---|---|---|
| 2,810,316 | 10/1957 | Snyder | 356/159 |
| 2,931,917 | 4/1960 | Beelitz | 356/159 |
| 2,941,087 | 6/1960 | Blumberg et al. | 356/167 |
| 3,513,247 | 5/1970 | Anderson et al. | 250/234 X |

*Primary Examiner*—Walter Stolwein
*Attorney, Agent, or Firm*—Beveridge, DeGrandi, Kline & Lunsford

[57] ABSTRACT

The present invention provides a measuring apparatus comprising at least four photocells adapted to be simultaneously, synchronously displaced in a common plane on respective linear paths for scanning a projected image of a zone to be measured, said paths being arranged to intersect at a single point whereby the photocells are caused to move radially relative to that point in scanning the image.

7 Claims, 1 Drawing Figure

U.S. Patent July 20, 1976 3,970,847
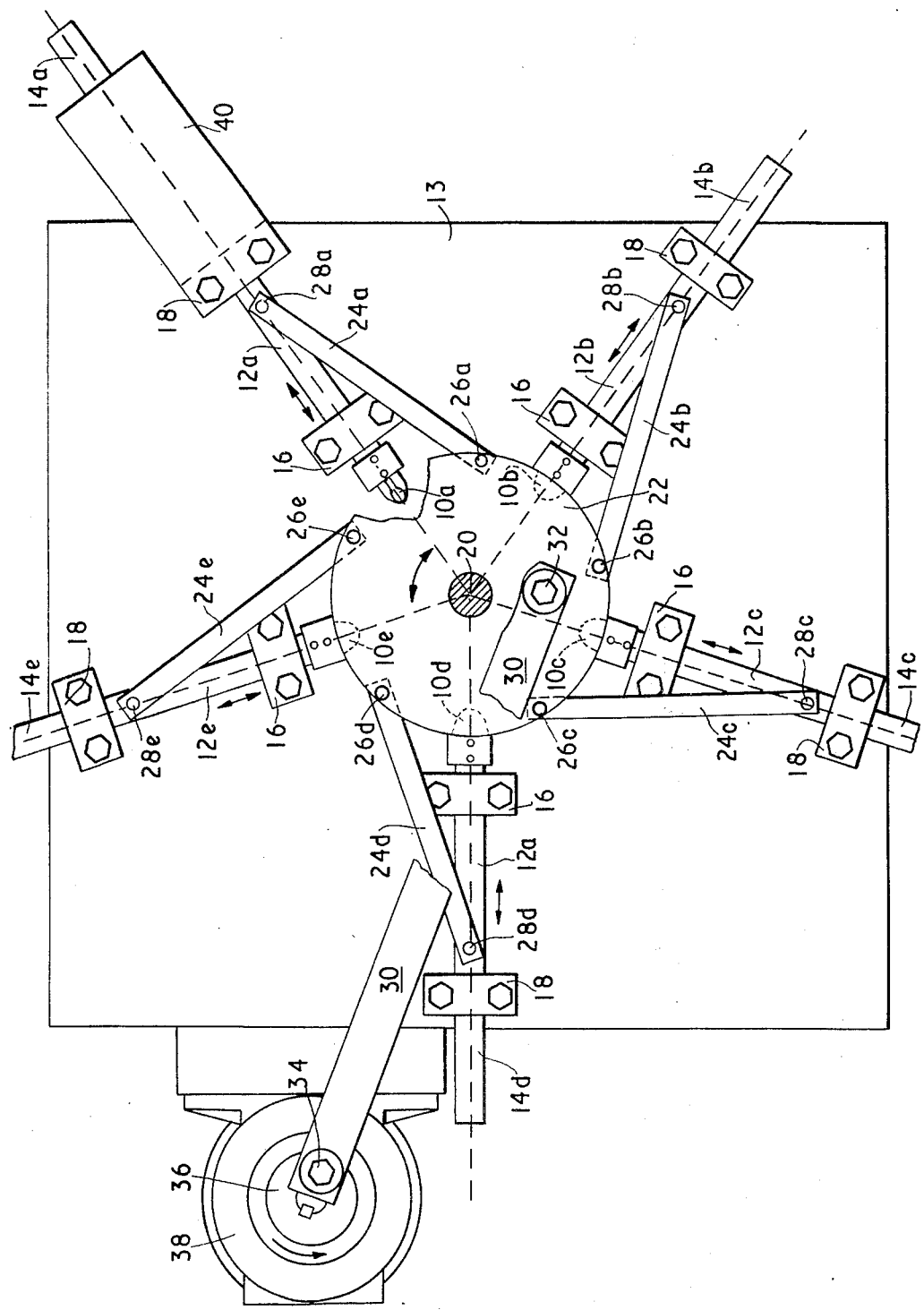

DIMENSION MEASURING APPARATUS

The invention relates to dimension measuring apparatus and is particularly concerned with such an apparatus for use primarily, but not exclusively, in measuring zone diameters on culture plates.

It is known in dimension measuring apparatus to utilise a single photocell to scan an image for the purpose or providing data from which zone dimensions can be calculated. However, in practice such an apparatus gives rise to a high proportion of meaningless results since, inter alia, it can produce no redundant information which can be used to check the accuracy of the result.

According to the present invention there is provided a measuring apparatus comprising at least four photocells adapted to be simultaneously, synchronously displaced in a common plane on respective similar paths for scanning a projected image of a zone to be measured, said paths being arranged to intersect at a single point whereby the photocells are caused to move radially relative to that point in scanning the image.

By the provision of four or more such photocells, preferably five, redundant information can be obtained which is subsequently sorted by computer software to give meaningful results.

The invention is described further hereinafter, by way of example, with reference to the accompanying drawing, which is a partially cut-away plan view of one embodiment of a measuring apparatus in accordance with the present invention.

The illustrated measuring apparatus includes five photocells 10a, 10b . . . 10e which are similarly mounted on respective sliders 12a, 12b . . . 12e, the sliders 12 being longitudinally displaceable relative to a base structure 13 along respective linear paths 14a, 14b . . . 14e in guides 16, 18 such that the photocells 10 are displaced in a common plane. The five paths 14a, 14b . . . 14e are arranged to meet at a single point 20 so that the displacement of the photocells 10 always takes place radially relative to the point 20.

The apparatus further includes a disc 22 which is mounted on the base structure 13 for rotation in a plane parallel to said common plane in which the photocells move and about an axis passing through the point 20. The disc 22 carries five link members 24a, 24b . . . 24e whose one ends are pivotally attached to the disc 22 at 26a, 26b . . . 26c, respectively. The other ends of the link members 24a, 24b . . . 24e are respectively pivotally connected to the sliders 12a, 12b . . . 12e at 28a, 28b . . . 28e.

The disc 22 is adapted to be reciprocably rotated through a predetermined angle by means of a crank arm 30 whose one end is pivotally connected to the disc at 32 and whose other end is pivotally connected, at an eccentric location 34, to a second disc 36 which is selectably rotatable by a motor and gearing 38.

By virtue of the aforegoing arrangement, angular rotation of the disc 22 is thus converted into linear displacement of the five photocells 10 along their respective paths 14, each photocell being displaced by an identical amount for a given rotation of the disc 22. A quantitative measurement of the linear photocell displacement is derived by means of a suitable transducer 40 which is connected to one of the sliders (in this case the slider 12a) and provides an electrical output indicative of the slider position.

The transducer output and the outputs of the five photocells 10 can be arranged to be applied to a computer which is programmed to produce a meaningful result from the input information.

A principal use of the above described apparatus is in measuring zone diameters on culture plates for antibiotic assay and similar processes. In this instance the apparatus additionally includes a programmable carriage for carrying and positioning a culture plate to be examined, a conventional light source and a projection system adapted to form an aerial image of a selected zone on the culture plate in said common plane of the five photocells 10, and a computer for controlling the operation of the apparatus and calculating the results.

The culture plate carriage (not shown) positions the zones for projection by the optical system. Either the carriage can be arranged to scan a predetermined rectilinear array or a programme if locations can be fed in from paper tape.

The photocells 10 are arranged to be moved radially inwardly from a position outside the edge of the image region towards the centre thereof. When the photocells 10 move in towards the image area, the first two photocells which encounter a zone edge are arranged to be ignored but readings are taken from the other three. The computer is arranged to calculate the diameter from the latter-readings without further reference to the position of the zone centre, provided it is within an allowable circle of error. The result is checked for size and position on the plate, then stored until the plate reading is complete. Out of range results are remeasured up to three times, failing which a zero result is returned. Thus, if the diameter cannot be calculated from the readings taken, a zero output will be provided.

The calculation of results includes an analysis of variance by row and column to validate the plate and a further test to eliminate spurious values, assumed to be those lying outside three sigma limits from the mean for each sample. Potency ratio and parallism are calculated, factors may be entered before or after the plate measurement, and final results are printed out.

Inter alia, advantages provided by the above described apparatus are that (1) overlapping zones, splashes and other imperfections can be ignored; (2) central spots do not affect readings; (3) the precise position of the zone centre is not relied upon; and (4) the circular part of a zone is assessed.

In the apparatus described, the number of photocells 10 is not critical but five is probably the optimum number. It is a feature of the apparatus that redundant information is provided by the photocells which is subsequently sorted by the computer software to give meaningful results. Two photocells moving on a diameter would give a result but no redundancy; three photocells would give a result even when not on diameters and with no restriction as to the center position, but would give no redundancy; four and more photocells give redundancy but an odd number allows the sample to be turned through 180° or 90° to get another independent reading on the zone to be measured. A large number of photocells gives great inaccuracy if those close together are selected by the software. Thus, it is found that the optimum number of photocells is probably five.

The particular manner described above for displacing the photocells along their paths 14a, 14b . . . 14e is by way of example only and clearly there are a large number of alternative mechanical and electrical arrangements possible for achieving the same result.

Furthermore, the apparatus can be used for office purposes, such as, for example, measuring the peak heights on charts or any other dimensions within its range.

I claim:

1. A measuring apparatus comprising at least four photocells, means mounting said photocells for synchronous, simultaneous displacement in a common plane for scanning a projected image of a zone to be measured, means constraining the photocells to move along respective, similar paths which project to a single point such that said photocells are caused to move substantially radially relative to that point in scanning the image, and a mechanism for synchronously reciprocating said photocells along said paths, said mechanism including a common, angularly reciprocable member, means mounting said member for angular displacement in a plane parallel to said common plane and about an axis passing through said single point, means for angularly reciprocating said common member in said parallel plane about said axis, and a respective linkage connecting said common member to each photocell mounting means whereby movement of said common member is transmitted to said photocell mounting means.

2. An apparatus according to claim 1, including respective sliders carrying said photocells, said constraining means being adapted to constrain said sliders to move along respective linear paths, and said linkages respectively connecting said sliders to said common member.

3. An apparatus according to claim 1 further comprising transducer means arranged to provide a signal indicative of the radial position of one of the photocells relative to said point and hence of the radial positions of all of the photocells relative to that point.

4. An apparatus according to claim 1 in which the means for angularly reciprocating said common member comprises a crank and drive means for said crank.

5. An apparatus according to claim 4 in which said common member is in the form of a disc.

6. An apparatus according to claim 5 in which each said linkage comprises a single rod pivotably connected at its two ends to the associated slider and the disc respectively, the location of the pivotable connections between the rods and the disc being such that angular reciprocation of the disc causes the sliders to be displaced linearly along said paths.

7. A measuring apparatus comprising at least four photocells, a respective slider means carrying each of said photocells, for displacement in a common plane to scan a projected image of a zone to be measured, means constraining the sliders for displacement such that the photocells move along respective, similar paths which project to a single point whereby said photocells are caused to move radially relative to that point in scanning the image, and a mechanism for synchronously reciprocating said photocells along said paths, said mechanism including a common, angularly reciprocable member, means mounting said member for angular displacement in a plane parallel to said common plane and about an axis passing through said single point, means for angularly reciprocating said common member in said parallel plane about said axis, and a respective linkage connecting said common member to each slider means and a transducer means arranged to provide a signal indicative of the radial position of one of the sliders relative to said point and hence of the radial positions of all of the photocells relative to that point.

* * * * *